United States Patent [19]

Frye

[11] Patent Number: 5,245,938
[45] Date of Patent: Sep. 21, 1993

[54] SOLID, PLIABLE ORGANIC COMPOUND FOR HOT/COLD THERMAL PADDING MATERIAL

[76] Inventor: Ruth E. Frye, 505 S. Main St., Lindsay, Okla. 73052

[21] Appl. No.: 793,604

[22] Filed: Nov. 18, 1991

Related U.S. Application Data

[63] Continuation-in-part of Ser. No. 499,624, Mar. 26, 1990, Pat. No. 5,066,411.

[51] Int. Cl.$^5$ ............... A61F 7/08; A61F 7/10; C09K 3/18
[52] U.S. Cl. ............... 112/441; 165/10; 252/70; 428/76; 428/225; 428/246; 428/260; 607/114; 607/108
[58] Field of Search ............... 128/399, 402, 403; 165/10; 252/70; 112/441; 428/76, 225, 246, 260

[56] References Cited

U.S. PATENT DOCUMENTS

| | | | |
|---|---|---|---|
| 3,871,376 | 3/1975 | Kozak | 128/403 |
| 4,462,224 | 7/1984 | Dunshee et al. | 128/403 |
| 4,596,250 | 6/1986 | Beisang et al. | 128/403 |
| 4,756,311 | 7/1988 | Francis | 128/403 |
| 5,066,411 | 11/1991 | Frye | 252/70 |

FOREIGN PATENT DOCUMENTS 257720 3/1988 European Pat. Off.
79991 4/1986 Japan.

*Primary Examiner*—James C. Cannon
*Attorney, Agent, or Firm*—Dennis T. Griggs

[57] ABSTRACT

An organic thermal reservoir padding material containing a hydroxyalkylcellulose compounded with an alkylene glycol yields a dry, consolidated core material. Best results are obtained in a formulation comprising about 4 parts by volume of hydroxyethylcellulose and about 3 parts by volume of propylene glycol. The resultant organic compound (Table I) is non-toxic, solid, non-tacky, dry and moldable into a solid structural form. A freeflowing, unconsolidated thermal reservoir material is produced by mixing about 2 parts by volume hydroxyethylcellulose with about 1 part by volume propylene glycol and about ¼ part by volume bicarbonate of soda.

6 Claims, 3 Drawing Sheets

SOLID, PLIABLE ORGANIC COMPOUND FOR HOT/COLD THERMAL PADDING MATERIAL

CROSS REFERENCE TO RELATED APPLICATION

This application is a continuation-in-part of U.S. application Ser. No. 07/499,624, filed Mar. 26, 1990, now U.S. Pat. No. 5,066,411.

FIELD OF THE INVENTION

The present invention relates generally to body-warming and body-cooling devices and in particular to passive thermal energy storage materials for use in such devices.

BACKGROUND OF THE INVENTION

Body-warming and body-cooling devices are known for application to a portion of a body, such as hands, head, ears and back to provide Warmth or cooling for comfort and for therapeutic purposes. For example, heating pads, ice packs and cold compresses are used for such purposes. Some hot and cold packs include a liquid solution or gel material sealed within a flexible container for storing thermal energy. Such containers may burst in response to overheating. In the event the container should rupture, the hot liquid or gel material will leak and may cause burn injury to the user. Moreover, in the event such a liquid or gel material should be used in a cold pack, there is a risk that the container may rupture upon being frozen, thereby permitting the liquid or gel material to leak upon thawing.

DESCRIPTION OF THE PRIOR ART

Examples of hot and cold pack devices which disclose a liquid or gel material sealed within a container are disclosed in the following U.S. patents:

| | | |
|---|---|---|
| 1,964,655 | 2,203,591 | 2,403,676 |
| 2,375,087 | 2,515,298 | 2,547,886 |
| 2,697,424 | 2,715,315 | 2,749,914 |
| 2,783,806 | 3,092,112 | 3,349,825 |
| 3,871,376 | 3,885,403 | 4,462,224 |
| 4,596,250 | 4,694,829 | 4,756,311 |

The prior art discloses various structures in which the thermal reservoir material may be packaged, such as a jacket (U.S. Pat. No. 2,403,676), and various shapes that the envelope container may take, such as a compressed shape to conform to the forehead of a person (U.S. Pat. No. 1,964,655), and a glove (U.S. Pat. No. 2,515,298).

A limitation on the use of such conventional body-warming and body-cooling devices is that a sealed container must be provided, and the liquid or gel material is subject to leakage should the container rupture or be punctured. Some thermal storage materials are toxic or corrosive. Moreover, the liquid or gel thermal material is not capable of maintaining a desired form or structure, and must be encapsulated or otherwise supported by a rigid container to maintain a desired shape.

Accordingly, a need exists for a dry, thermal reservoir material which may be frozen or heated and which will not burst, explode, burn, melt or drip when heated to above the boiling point of water, or cooled below the freezing point of water. Moreover, a thermal reservoir material is needed which can be molded into various structural forms, and which will maintain its molded form after curing, making it suitable for body-cooling as well as body-warming applications. A dry thermal reservoir fabric material suitable for both hot and cold service, which is soft and pliable, as well as being non-toxic, is needed for use in combination with various items, for example, earmuffs, hats, gloves, socks, shoes, boots, coats, stuffed toys, pillows, beverage coolers, food warmers, refrigerated chests, heating pads, cooling pads, blankets, quilts and the like.

OBJECTS OF THE INVENTION

It is, therefore, the principal object of the present invention to provide an improved thermal reservoir material which may be frozen or heated and which will not burst, explode, burn, melt or drip when heated to above the boiling point of water, or cooled below the freezing point of water.

Another object of the invention is to provide an improved thermal reservoir material which can be molded into various structural forms, and which will maintain its molded form after curing.

Yet another object of the present invention is to provide a thermal reservoir fabric material which can be used for body-cooling as well as body-warming applications.

Another object of the invention is to provide a dry thermal reservoir fabric material suitable for both hot and cold service which is soft and pliable.

Still another object of the invention is to provide an improved dry thermal reservoir material of the character described, which can be used as a particulated padding material.

Yet another object of the invention is to provide an improved dry thermal reservoir fabric material which is non-toxic.

SUMMARY OF THE INVENTION

The foregoing objects are satisfied by the present invention which provides an organic thermal reservoir material comprising (a) a hydroxy-$C_{1-5}$ alkyl-cellulose (preferably hydroxyethylcellulose) and (b) a $C_{2-5}$ alkylene glycol (preferably propylene glycol) or the condensation product thereof; the cured material provides a dry, solid core material. The composition may be molded into any desired shape and is non-toxic. More specifically, the organic thermal reservoir composition of the invention is produced by mixing about three parts by volume of propylene glycol with about four parts by volume of hydroxyethylcellulose. During the reaction, an OH group on a carbon atom of the hydroxyethylcellulose molecule condenses with an OH group on the propylene glycol molecule. Water ($H_2O$) is a reaction by-product which is removed during curing. The resultant organic compound is non-toxic, solid, non-tacky, dry and moldable into a solid, pliable structural form.

An unconsolidated thermal padding material is produced by mixing about 2 parts by volume hydroxyethylcellulose with about 1 part by volume propylene glycol and about ¼ part by volume bicarbonate of soda. The bicarbonate of soda causes the compound to particulate, thereby producing a thermal reservoir stuffing material for various clothing applications.

A low density thermal reservoir material is provided by combining about 1 part by volume hydroxyethylcellulose with 1½ parts by volume propylene glycol, ¼ part by volume 1,1'-azodicarbonamide (a blowing agent), preferably CELOGEN trademark of Uniroyal Chemical Company, and ¼ part by volume CARBOPOL ®, a blend of water soluble resins having gel forming properties, manufactured by B.F. Goodrich Chemical Company. This yields a non-toxic, lightweight thermal reservoir material which may be attached to fabric material by various methods, for example, by stitching, stapling, adhesives and thermal welding.

A liquified formulation which can be used as a coating for a thread or fabric is provided by combining about 2 parts by volume hydroxyethylcellulose with about ¾ part propylene glycol, 1/26 part by volume bicarbonate of soda and 1/13 part CELOGEN. The liquid formulation penetrates the fibers of the thread, and upon curing, the thread is encapsulated by a tubular jacket of the thermal reservoir material. The thread is then woven to produce a fabric having good heat retention capability.

BRIEF DESCRIPTION OF THE DRAWINGS

Other features and advantages of the present invention will be appreciated by those skilled in the art upon reading the detailed description which follows in connection with the attached drawings, wherein.

DETAILED DESCRIPTION OF THE PREFERRED FORMULATION

Figure 1:
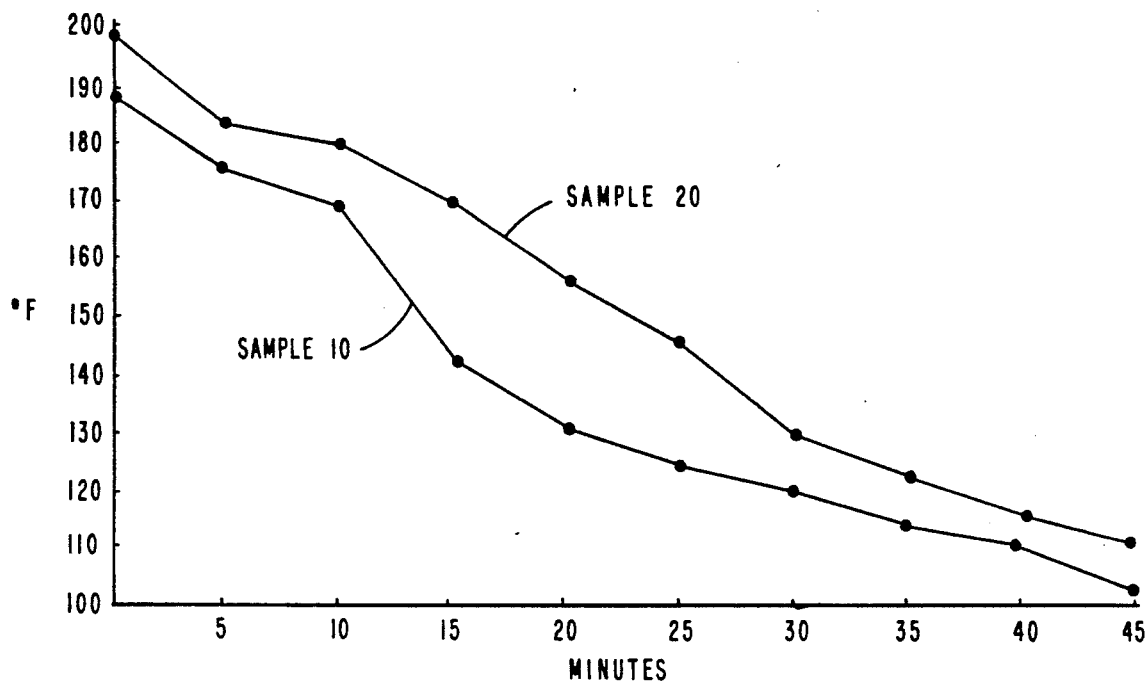
FIG. 1 is a graph of sample temperature (°F.) as a function of time which represents the heat retention capabilities of first and second sample compositions of the preferred formulation.

The present invention provides an organic thermal reservoir composition which includes, as its active ingredients, hydroxyethylcellulose and propylene glycol. Satisfactory results for molded applications have been obtained by compounding from about 20% to about 40% part by volume of propylene glycol with about 60% to about 80% part by volume of hydroxyethylcellulose. The best results for molded applications have been obtained by compounding three parts by volume of propylene glycol with four parts by volume of hydroxyethylcellulose.

Other cellulose derivatives may be used to good advantage in the formulation of the present invention, for example, hydroxypropylcellulose and other glycols, for example, ethylene glycol may be used in substitution for propylene glycol. The preferred formulation of the present invention comprises generally (a) a hydroxyalkylcellulose containing 1 to 5 carbon atoms in the alkyl radical and (b) an alkylene glycol containing 2 to 5 carbon atoms in the alkyl radical, or a condensation product of components (a) and (b).

The preferred formulations for molded (consolidated) embodiments of the present invention are combined in the following proportions:

| VOLUME PERCENT - CONSOLIDATED | | | |
|---|---|---|---|
| COMPONENT | SUITABLE | PREFERRED | MOST PREFERRED |
| PROPYLENE GLYCOL | 20-40 | 25-35 | 25 |
| HYDROXYETHYL-CELLULOSE | 60-80 | 65-75 | 75 |

The preferred formulation yielded by the reaction of the foregoing components is shown in Table I.

The composition of the consolidated embodiment is preferably made in a batch process as follows: The ingredients are placed in a vessel such as a stainless steel mixing tank. Hydroxyethylcellulose powder is placed in the tank and then liquid propylene glycol is poured into the tank in the preferred proportions as set forth above. The mixture is then agitated by suitable means such as a stirrer. Stirring is continued until a smooth, homogenous mixture is obtained. Thereafter, the mixture is placed in a suitable container having a desired form, or in the cavity of a mold. The mixture is then cured by baking in an oven at 110°-170° F. (43° C.-76° C.) until the water by-product has been substantially removed. Alternatively, the mixture is cured by irradiating it in a microwave oven.

According to an unconsolidated embodiment, the reaction mixture of propylene glycol with hydroxyethylcellulose does not require the application of heat or curing. The resulting mixture has a dry, crumbly consistency and has an average size comparable to the size of bread crumbs. This dry, unconsolidated mixture is well suited for use as a stuffing material. Best results for producing an unconsolidated crumbly mixture for stuffing applications has been obtained by compounding one part by volume of propylene glycol with two parts by volume of hydroxyethylcellulose.

The preferred formulations for the dry, unconsolidated stuffing material embodiment of the present invention are combined in the following proportions:

| VOLUME PERCENT - UNCONSOLIDATED | | | |
|---|---|---|---|
| COMPONENT | SUITABLE | PREFERRED | MOST PREFERRED |
| PROPYLENE GLYCOL | 25-40 | 25-35 | 33 |
| HYDROXYETHYL-CELLULOSE | 60-75 | 65-75 | 67 |

REFERENTIAL EXAMPLES

In order to provide a better understanding of the present invention including representative advantages and limitations thereof, the following referential examples are offered as related to certain tests performed in the practice of this invention, and illustrate the excellent heat retention and cold retention properties of the preferred formulations, as follows:

EXAMPLE 1

A 42 gram (1.5 oz) sample 10 of the preferred formulation was prepared by reacting three parts by volume of propylene glycol with four parts by volume of hydroxyethylcellulose. The sample was cured and thereafter shrink wrapped in one thickness of 0.52 mil (0.013 mm) plastic film. The bulb of a mercury thermometer was embedded within the sample. The temperature within the test facility was maintained constant at 74° F. (23° C.) throughout the test, and was free from draft.

The sample 10 was heated in an oven until an initial temperature of 188° F. (86° C.) was produced as illustrated by the curve 10 in FIG. 1. It was then allowed to cool at room temperature (74° F., 23° C.) and the rate of cooling was determined by recording the indicated temperature of the sample at 5 minute intervals during a 45 minute period.

After 5 minutes, the sample 10 had cooled to 176° F. (80° C). After 10 minutes, the indicated temperature of sample 10 was 170° F. (76° C.). The most substantial decline occurred during the interval 10 minutes to 15 minutes, in which the temperature dropped by 28° F. (-2° C.) to 142° F. (61° C.). The decline remained consistent with no more than a 4° F. decline per 5 minute interval during the remainder of the test. After 45 minutes had elapsed, the temperature of sample 10 had dropped to 102° F. (39° C.).

The sample 10 was tested a total of 6 times, with the temperature measurements being recorded at 5 minute intervals during each test. Each time, the sample 10 was heated to an initial temperature of about 187° F. (86° C.), with the indicated temperatures of the respective readings varying by no more than about 3° F., and having an average variation of about 1° F. per reading.

In summary, sample 10 decreased in temperature by a total of 86° F. (30° C.) in 45 minutes or at an average rate of 1.9° F. per minute. The average rate of heat loss was at a rate of 1.1° F. per minute during the last 25 minutes of the test.

EXAMPLE 2

The curve designated 20 in FIG. 1 represents the rate of heat loss for a 42 gram (1.5 oz) sample 20 of the preferred mixture of propylene glycol and hydroxyethylcellulose in the proportions as set forth in Example 1. The sample 20 was blended and cured following the same procedure of Example 1. The sample 20 was first wrapped in a single thickness of 0.125 inch (3 mm) poly fill plastic film, and was then wrapped with two thicknesses of 0.52 mil (13 mm) plastic film. The sample 20 was heated for 40 seconds in a microwave oven to a temperature of 198° F. (92° C.).

The sample 20 was tested a total of 6 times, with the temperature measurements being recorded at 5 minute intervals. Each time, the sample 20 was heated to an initial temperature of about 198° F. (92° C.), with the indicated temperatures of the respective readings varying by no more than about 3° F. per reading, and having an average variation of about 1° F. per reading.

It will be noted that the average rate of heat loss of sample 20 was substantially lower during the interval of 10 minutes to 30 minutes as compared with the sample 10 which had only a single wrapping of plastic film.

EXAMPLE 3

Figure 2:
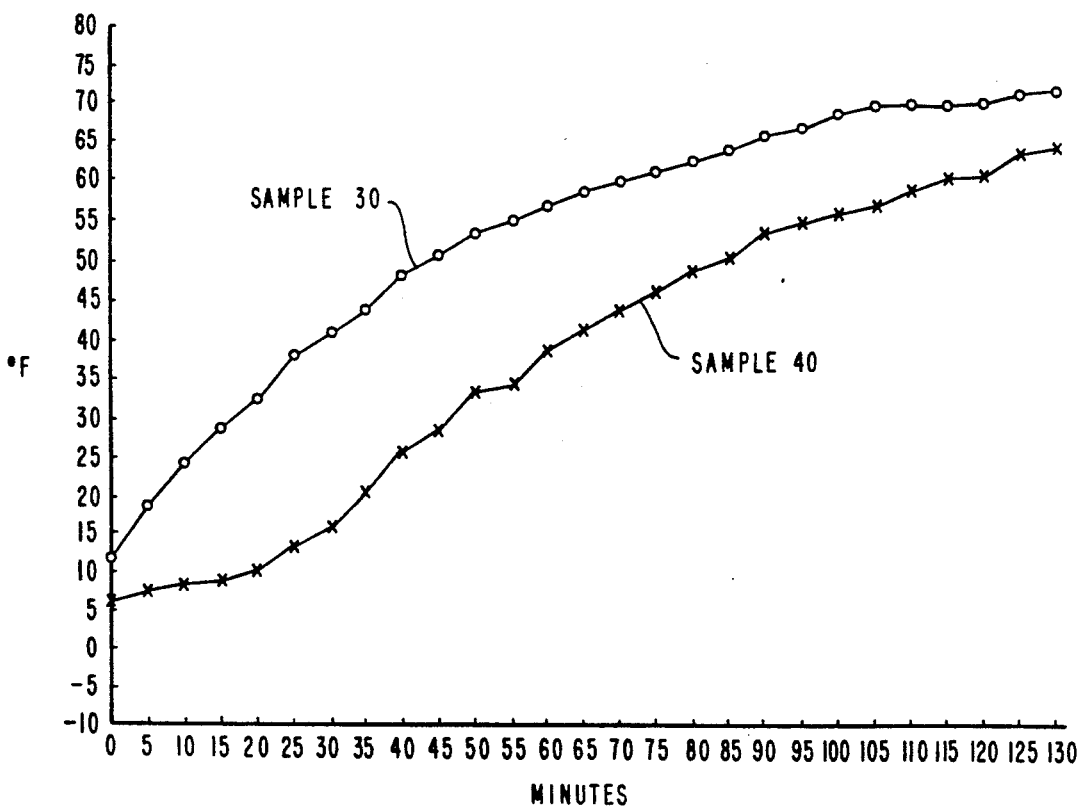
FIG. 2 is a graph of sample temperature (°F.) as a function of time which illustrates the cold retention properties of said first and second sample compositions.

Referring to FIG. 2, a 5 ounce (140 grams) sample 30 of the preferred formulation was prepared by reacting three parts by volume of propylene glycol with four parts by volume of hydroxyethylcellulose as set forth above in Example 1. Ambient temperature was maintained constant at 85° F. (29° C.). The temperature reading was taken at 5 minute intervals with a thermometer embedded within the sample 30. The performance of the cured formulation given above is indicated by the curve 30. The sample was initially cooled to a temperature of 12° F. (-11° C.), and was then placed in a room at ambient 85° F. (29° C.) which was free from draft.

The curve 30 shows that the average rate of heat gain was 0.7° F. per minute during the first 60 minutes of the test, and was only 0.25° F. per minute during the next 60 minutes of the test.

The sample 30 was tested a total of 6 times, with the temperature measurements being recorded at 5 minute intervals. Each time, the sample 30 was cooled to an initial temperature of about 12° F. (-11° C.), with the indicated temperatures of the respective readings varying by no more than about 3° F. per reading, and having an average variation of about 1° F. per reading.

EXAMPLE 4

Referring again to FIG. 2, a 5 ounce (140 grams) sample 40 was prepared by adding one part by volume purified water to two parts by volume propylene glycol and four parts by volume of hydroxyethylcellulose. The sample was not cured, but was instead immediately chilled to a temperature of 6° F. (-14° C.).

The average rate of heat gain during the first 60 minutes of the test for sample 40 was 0.55° F. per minute, and the average rate of heat gain during the second 60 minutes was 0.35° F. per minute.

The sample 40 was tested a total of 6 times, with the temperature measurements being recorded at 5 minute intervals. Each time, the sample 40 was cooled to an initial temperature of about 5° F. (-15° C.), with the indicated temperatures of the respective readings varying by no more than about 3° F. per reading, and having an average variation of about 1° F. per reading.

The room temperature in which the sample 40 tests were conducted was maintained constant at 85° F. (29° C.).

EXAMPLE 5

Figure 3:
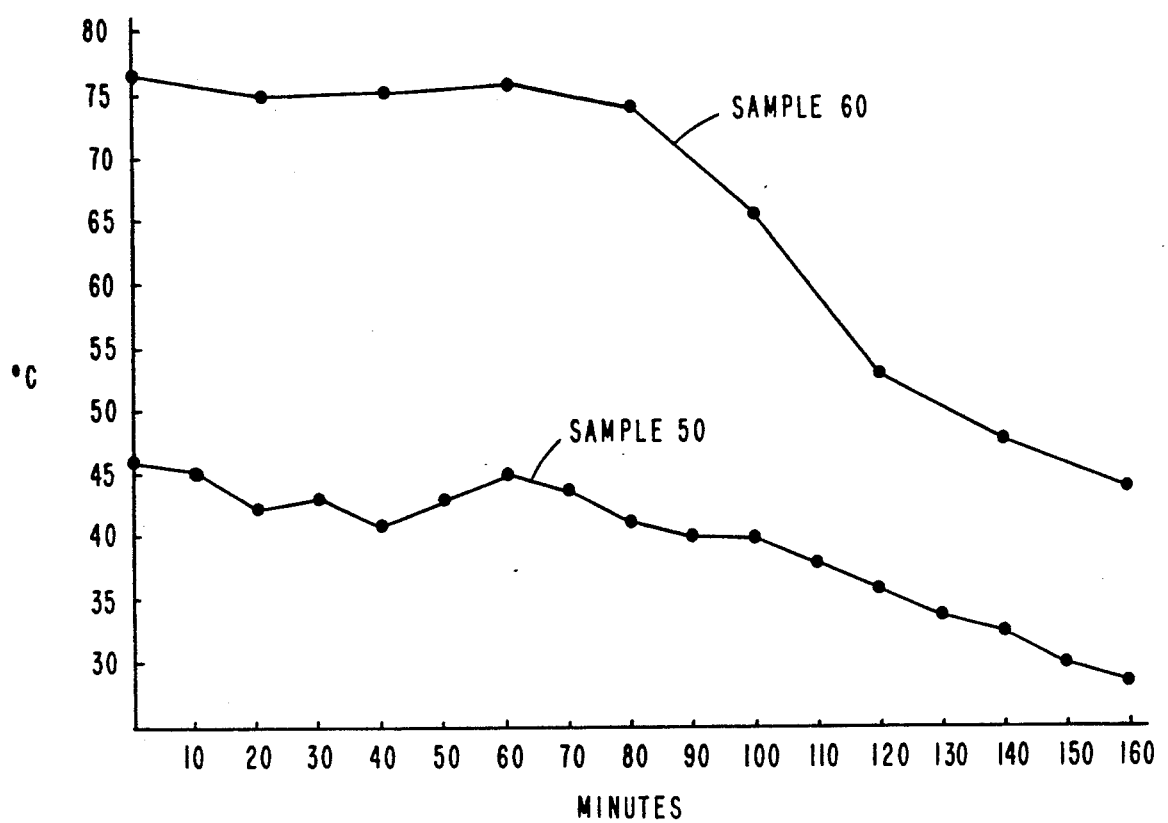
FIG. 3 is a graph of sample temperature (°C.) as a function of time showing the heat retention characteristics of the first and second sample compositions including internal and external insulation means.

Referring now to FIG. 3, a 4 ounce (112 grams) sample 50 of the preferred formulation was prepared according to the method and proportions given in Example 1. The sample 50 was insulated on one side by a fabric jacket having a thickness of approximately 5 mils (0.125 mm) to simulate a heat pad. The curve designated 50 in FIG. 3 illustrates the heat loss performance of sample 50 when used as a heat pad. The exposed side of the heat pad was placed onto the body of a subject having a body weight of 185 pounds (83 kg) and a body temperature of 98.6° F. (37° C.). The heat pad sample 50 was applied to the subject immediately after removal from the oven. The temperature reading was taken every 5 minutes. The room temperature was maintained constant at 77° F. (25° C.).

The sample 50 was tested a total of 6 times, with the temperature measurements being recorded at 10 minute intervals. Each time, the sample 50 was heated to an initial temperature of about 115° F. (46° C.), with the indicated temperatures of the respective readings varying by no more than about 2° C. per reading, and having an average variation of less than 1° C. per reading.

The average rate of heat loss for the heat pad sample 50, while placed in contact with a subject having a body temperature of 98.6° F. (37° C.), was 0.1° C. per minute.

EXAMPLE 6

Referring again to FIG. 3, a sample 60 was prepared using the preferred proportions set forth above, and was molded in the shape of a rectangular pad. The pad sample 60 was sandwiched between two sheets of styrofoam having a thickness of 0.75 inch (19 mm). A thermometer was embedded within the sample.

The heat loss was negligible during the first 80 minutes of the test. The sample 60 temperature dropped substantially at an average rate of 0.38° C. per minute during the last 80 minutes of the test.

The sample 60 was tested a total of 6 times, with the temperature measurements being recorded at 20 minute intervals. Each time, the sample 60 was heated to an initial temperature of about 171° F. (77° C.), with the indicated temperatures of the respective readings varying by no more than about 2° C. per reading, and having an average variation of less than about 1° C. per reading.

EXAMPLE 7

Figure 4:
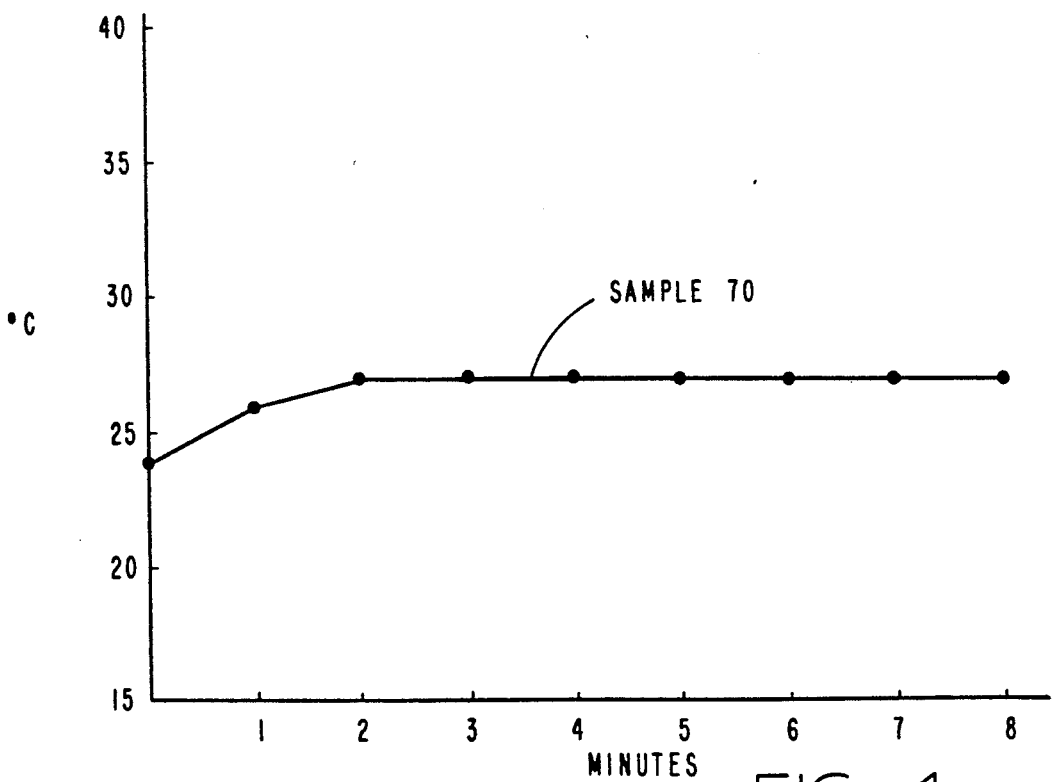
FIG. 4 is a graph of sample temperature (°C.) as a function of time within a water calorimeter during a determination of the specific heat of the organic thermal reservoir material of the preferred formulation.

Referring now to FIG. 4, a 5 gram (0.175 ounce) sample 70 of the preferred formulation was prepared according to the procedure and proportions of Example 1. The sample 70 was placed within a sealed metal container within 100 grams (3.5 ounce) of water in a water calorimeter. The water in the calorimeter and the sample 70 was preheated to an initial temperature of 77° F. (25° C.). The temperature rise from about 77° F. (25° C.) to about 81° F. (27° C.) occurred over a 2 minute interval as indicated by the curve 70. Two hundred calories of thermal energy were input to the calorimeter to raise the temperature of the sample 70 from 77° F. (25° C.) to 81° F. (27° C.), thereby indicating a specific heat value of 20 for the preferred formulation.

EXAMPLE 8

In this example, a 5 ounce (140 grams) sample 80 of the preferred formulation was prepared according to the procedure and proportions of Example 1. Prior to curing, 1 ounce (28 grams) of particulated styrofoam was mixed with the 5 ounces (140 grams) of formulation. The 6 ounce (168 grams) sample 80 containing the particulated styrofoam was then cured in an oven as set forth in Example 1. The sample 80 was shrink wrapped in one thickness of 0.52 mil (13 mm) plastic film. The bulb of a mercury thermometer was embedded within the sample. The temperature within the test facility was maintained constant at 74° F. (23° C.) throughout the test, and was free from draft. The sample was heated in an oven to an initial temperature of 200° F. (93° C.). It was then allowed to cool at ambient room temperature 74° F. (23° C.). The sample 80 decreased in temperature at an average rate of 1.2° F. per minute, and was relatively linear as compared with the performance of samples 10 and 20.

EXAMPLE 9

A 5 ounce (140 grams) sample 90 of the preferred formulation was prepared according to the procedure and proportions set forth in Example 1. After curing the 5 ounce (140 grams) sample was particulated into irregular granules having an average length of 0.3 cm-0.5 cm. Five ounces (140 grams) of expanded, cellular polystyrene granules having substantially the same size (0.3 cm-0.5 cm) was then thoroughly mixed with the formulation granules. The 10 ounce (280 grams) mixture of formulation and polystyrene granules was then shrink wrapped in one thickness of 0.52 mil (13 mm) plastic film. The bulb of a mercury thermometer was embedded within the sample 90. The ambient temperature within the test facility was maintained constant at 74° F. (23° C.) throughout the test, and was free from draft.

The sample 90 was heated in an oven until an initial temperature of 180° F. (82° C.) was produced. The sample 90 was then allowed to cool at room temperature 74° F. (23° C.) and the rate of cooling was determined by reading the indicated temperature of the sample 90 at 5 minute intervals over a 45 minute period. The sample 90 decreased in temperature at an average rate of 0.9° F. per minute. The average rate of loss was at a rate of 0.6° F. per minute during the last 25 minutes of the test.

EXAMPLE 10

About 1 part by volume hydroxyethylcellulose and about ½ part by volume propylene glycol was mixed with about 2 parts by volume of polyester fibers. Upon curing, the result was a consolidated stuffing material which can be used as padding in various fabric products such as pillows, toys, quilts and the like.

EXAMPLE 11

An unconsolidated formulation was prepared to produce a thermal reservoir stuffing material. In this formulation, about 2 parts hydroxyethylcellulose was combined with about part propylene glycol and about ¼ part bicarbonate of soda. The resulting formulation was characterized by a free-flowing lumps or nodules having diameter sizes ranging from about 0.5 cm to about 1.5 cm. The free-flowing thermal reservoir nodules are useful as padding and stuffing material in various articles of clothing such as vests, mittens, scarfs, headbands, shoes, bedding and the like.

EXAMPLE 12

In this example, a consolidated formulation was prepared according to the procedure of Example 1 and with the following ingredients: about 1 part by volume hydroxyethylcellulose mixed with about 1½ parts by volume propylene glycol, about ¼ part by volume CELOGEN and about ¼ part by volume CARBOPOL ®. The resulting formulation was placed in a mold to form a solid layer upon curing.

EXAMPLE 13

In this example, a lightweight, consolidated formulation was prepared according to the procedure of Example 1 and with the following ingredients: about 1 part by volume hydroxyethylcellulose, about ¾ part by volume propylene glycol, about 1/26 part bicarbonate of soda and about 1/26 part by volume of a blowing agent, for example, 5-PHENYLTETRAZOLE manufactured by Uniroyal Chemical Company under the trademark EXPANDEX ®. The blowing agent produces closed air cells within the solid core, thereby reducing its weight and density.

EXAMPLE 14

A liquified formulation was prepared for application to textile fibers. This formulation was prepared according to the following proportions: about 2 parts by volume hydroxyethylcellulose, about ¾ part by volume propylene glycol, about 1/26 part bicarbonate of soda and 1/13 part 1,1'-azodicarbonamide, which is available from the Uniroyal Chemical Company under the trademark CELOGEN. The resulting liquified formulation can be mixed with fibers prior to spinning to produce thread. Alternatively, the liquid formulation can be applied as a coating to the thread, which after curing provides a jacket of thermal reservoir material about the thread.

Figure 5:
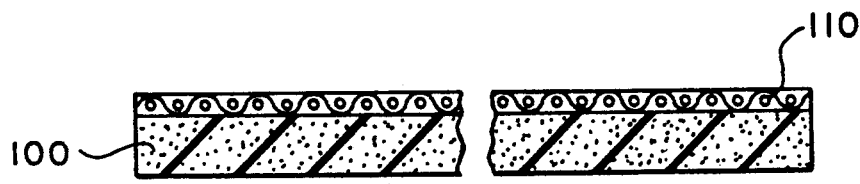
FIG. 5 is an enlarged sectional view of a layer of fabric material bonded to a layer of thermal reservoir material formulated according to the present invention.

Referring now to FIG. 5, a layer 100 of consolidated thermal reservoir material is bonded to a layer 110 of fabric material. Bonding may be obtained by an adhesive deposit, or by flame lamination.

Figure 6:
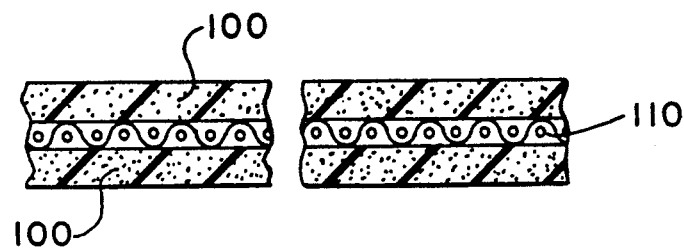
FIG. 6 is an enlarged sectional view of a layer of fabric material which is sandwiched between two layers of thermal reservoir material having the composition of the present invention.

Referring to FIG. 6, the layer 110 of fabric material is embedded within a unitary substrate of thermal reservoir material 100. Preferably, the thermal reservoir material is liquified and is applied as a coating to the fabric material 110, with the liquified thermal reservoir formulation penetrating the woven fabric material.

Figure 7:
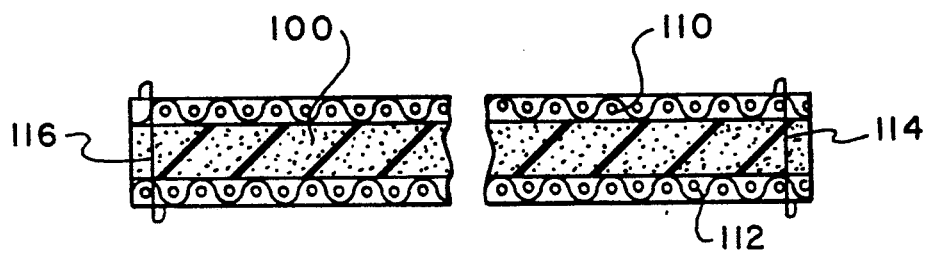
FIG. 7 is an enlarged sectional view of a core of thermal reservoir material sandwiched between first and second layers of fabric material, and being secured by stitching; and, FIG. 8 is a view similar to FIG. 7 in which the fabric layers are secured to the thermal reservoir material by a thermal weld.

Referring now to FIG. 7, a layer of consolidated thermal reservoir material is sandwiched between an upper fabric layer 110 and a lower fabric layer 112. The composite assembly is stabilized by stitches 114, 116.

Figure 8:
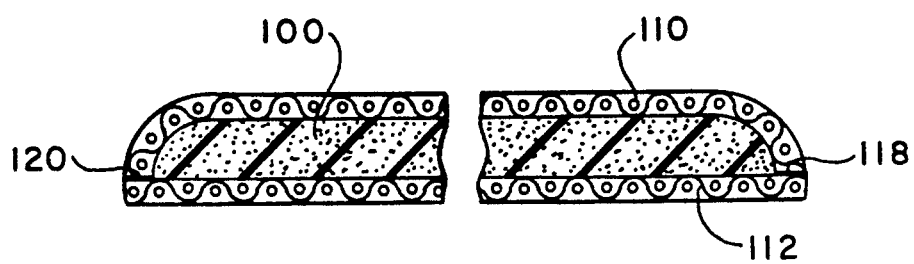

Referring now to FIG. 8, a layer 100 of thermal reservoir material is secured between first and second textile fabric layers 110, 112. The first and second textile layers are sealed together along the peripheral edges by thermal welds 118, 120.

Other consolidated formulations were prepared and tested, with the volume ratio of propylene glycol to hydroxyethylcellulose being varied through the range of 20%-40% for propylene glycol and 60%-80% for hydroxyethylcellulose. Marginal heat gain/heat loss performance was noted for the proportion 40% - propylene glycol, 60% hydroxyethylcellulose. The volume ratio proportion 40% - propylene glycol, 60% hydroxyethylcellulose. The ethylcellulose provided acceptable to good heat loss/heat gain performance. The best results for molded (unconsolidated) product applications, however, were provided by the volume ratio of 3 parts propylene glycol to 4 parts hydroxyethylcellulose. The resulting product, in all of the formulations, was curable to a dry, solid, pliable composition which was non-toxic and non-tacky.

Other stuffing (unconsolidated) formulations were prepared and tested, with the ratio of propylene glycol to hydroxyethylcellulose being varied through the range of 25-40 volume percent for propylene glycol and 60-75 volume percent for hydroxyethylcellulose. Marginal heat gain/heat loss performance was noted for the proportion 40% by volume propylene glycol, 60% by volume hydroxyethylcellulose. The volume ratio of 25%-35% propylene glycol and 65%-75% hydroxyethylcellulose provided acceptable to good heat loss/heat gain performance. The best results for stuffing material product applications, however, were provided by the volume ratio of about 1 part by volume propylene glycol to about 2 parts by volume hydroxyethylcellulose. The resulting product was dry, solid, unconsolidated, crumbly particles approximately the size of bread crumbs which were self-curing when reacted, and did not require heating.

The hydroxyethylcellulose used in the foregoing consolidated and unconsolidated formulations is preferably of cosmetic grade. Cosmetic grade hydroxyethylcellulose may be obtained from Aqualon Corporation of Wilmington, Delaware under the brand name Natrasol ™. The propylene glycol utilized in the foregoing formulations is preferably purified and non-toxic food grade. It can be obtained from commercial suppliers of chemical formulations, for example, Ashland Chemical Company of Dallas, Tex.

The cold retention properties of the molded product application formulations were improved by adding purified water and then freezing the formulation instead of curing it. The enhanced cold retention formulation which included purified water was subject to leakage upon thawing. The heat retention capability of the formulations was enhanced by blending a thermal insulation material such as styrofoam in the formulation before curing, or within the particulated formulation after curing.

The compositions of the present invention have proven effective as a thermal reservoir material for body-warming and body-cooling devices. The compositions can be used with or without any type of outside container or envelope, and can be used in combination with various conventional body-warming and body-cooling products, including, but not limited to earmuffs, hats, gloves, socks, shoes, boots, coats, terry cloth garments, head and neck scarves and also in a wide variety of stuffed products including, but not limited to toys and pillows, as well as therapeutic devices such as back braces, heating pads, hot compresses and cold compresses. The consolidated formulation can be poured into a mold, and after being heated and cooled, retains its size and shape during both hot and cold service. Moreover, the consolidated formulation can be formed in sheets or layers and applied as a lamination to fabric material as shown in FIGS. 5, 7 and 8. Additionally, fabric material can be embedded within the consolidated formulation prior to curing as shown in FIG. 6, thereby producing a composite material having good heat retention and may be used to good advantage, for example, in the construction of quilts and blankets.

The components of the foregoing formulations are nontoxic, are biodegradable, and can be heated to a desired temperature in a microwave oven or frozen to temperatures well below zero without damage or performance degradation. Accordingly, the formulations of the present invention are safe for use in consumer products, and in particular for products intended for use by children. Moreover, the consolidated formulation can be molded into any desired shape, thereby making it well suited for diverse applications, for example, heated and chilled beverage holders.

The above volume ratios and reaction conditions have been provided for illustration purposes only. As those skilled in the art will recognize, it is likely that acceptable thermal reservoir material can be produced using reaction ratios and conditions different from the preferred values given above.

I claim:

1. A composite thermal padding material suitable for body-warming as well as body-cooling applications including a first substrate of fabric material and a second substrate of dry thermal reservoir material which will not burst, explode, burn, melt or drip when heated to above the boiling point of water or cooled below the freezing point of water and which is moldable into structural forms which are self-maintaining after curing, wherein the first substrate of fabric material is superposed onto the second substrate of dry thermal reservoir material, and being secured thereto, wherein the dry thermal reservoir material comprises (a) a hydroxyalkylcellulose containing 1 to 5 carbon atoms in the alkyl radical and (b) an alkylene glycol containing 2 to 5 carbon atoms in the alkyl radical, or a condensation product of components (a) and (b).

2. A composite thermal reservoir padding material suitable for body-warming as well as body-cooling applications comprising a layer of textile fabric embedded within a core of dry thermal reservoir material which will not burst, explode, burn, melt or drip when heated to above the boiling point of water or cooled below the freezing point of water and which is moldable into structural forms which are self-maintaining after curing comprising (a) a hydroxyalkylcellulose containing 1 to 5 carbon atoms in the alkyl radical and (b) an alkylene glycol containing 2 to 5 carbon atoms in the alkyl radical, or a condensation product of components (a) and (b).

3. A composite thermal reservoir padding material suitable for body-warming as well as body-cooling applications including first and second substrates of a textile fabric material, and a solid core layer of dry thermal reservoir material which will not burst, explode, burn, melt or drip when heated to above the boiling point of water or cooled below the freezing point of water and which is moldable into structural forms which are self-maintaining after curing sandwiched between the first and second substrates, the thermal reservoir material comprising (a) a hydroxyalkylcellulose containing 1 to 5 carbon atoms in the alkyl radical and (b) an alkylene glycol containing 2 to 5 carbon atoms in the alkyl radical, or a condensation product of components (a) and (b).

4. A composite thermal reservoir material as defined in claim 3, wherein the first and second textile fabric layers are secured to the solid core thermal reservoir layer by a stitched thread.

5. A composite thermal reservoir padding material as defined in claim 3, wherein the first and second textile layers are secured to the thermal reservoir core layer by adhesive bonding.

6. A composite thermal reservoir padding material as defined in claim 3, wherein the first and second textile layers are sealed by a thermal weld.

* * * * *